United States Patent [19]

Katner et al.

[11] 4,338,452
[45] Jul. 6, 1982

[54] 1-AND 2-(1-ALKYL-1H-TETRAZOL-5-YL-METHYL)-1H-TETRAZOL-5-THIOLS AND 1-CYANOMETHYL TETRAZOLE-5-THIOL

[75] Inventors: Allen S. Katner; Stephen J. Bogard, both of Indianapolis, Ind.

[73] Assignee: Eli Lilly and Company, Indianapolis, Ind.

[21] Appl. No.: 187,861

[22] Filed: Sep. 17, 1980

[51] Int. Cl.³ .................. C07D 257/04; A61K 31/43; A61K 31/545
[52] U.S. Cl. .................... 548/251; 424/269; 424/246; 424/271; 544/27
[58] Field of Search .......................... 548/251; 544/27

[56] References Cited

U.S. PATENT DOCUMENTS

| | | | |
|---|---|---|---|
| 2,386,869 | 10/1945 | Kendall | 548/251 |
| 3,767,667 | 10/1973 | Kamiya et al. | 548/251 |
| 4,080,498 | 3/1978 | Numata et al. | 544/27 |
| 4,110,338 | 8/1978 | Kamiya et al. | 548/251 |
| 4,238,608 | 12/1980 | Numata et al. | 544/27 |

FOREIGN PATENT DOCUMENTS 2650231  5/1978  Fed. Rep. of Germany ...... 424/269

Primary Examiner—David B. Springer
Attorney, Agent, or Firm—William B. Scanlon; Arthur R. Whale

[57] ABSTRACT

Tetrazole thiols represented by the formulae

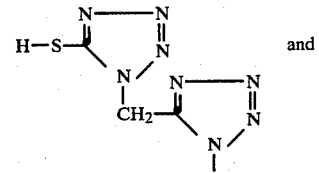

and

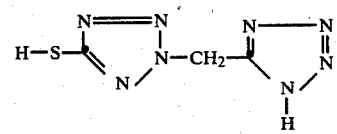

and the $C_1$–$C_3$ alkyl derivatives thereof are provided. The tetrazole thiols are useful in the preparation of broad spectrum cephalosporin antibiotics.

7 Claims, No Drawings

1- AND 2-(1-ALKYL-1H-TETRAZOL-5-YL-METHYL)-1H-TETRAZOL-5-THIOLS AND 1-CYANOMETHYL TETRAZOLE-5-THIOL

SUMMARY OF THE INVENTION

This invention relates to heterocyclic thiols. In particular, it relates to isomeric bis-tetrazolemethyl thiols represented by the following formulas:

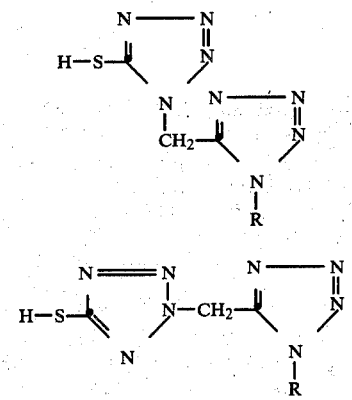

wherein R is hydrogen or $C_1$–$C_3$ alkyl, and to 1-cyanomethyl-1H-tetrazole-5-thiol useful as an intermediate in the preparation of the bis-tetrazoles of the above formula A.

The 1-(1H-tetrazol-5-ylmethyl)-1H-tetrazole-5-thiols of the above formula A wherein R is hydrogen are prepared by the reaction of 1-cyanomethyl-1H-tetrazole-5-thiol and tetramethylguanidinium azide. The compounds of the formula A wherein R is $C_1$–$C_3$ alkyl are prepared by reacting an ester of 5-chloro-1H-tetrazol-1-ylacetic acid with a $C_1$–$C_3$ alkyl amine to form the corresponding 5-chloro-1H-tetrazole-1-yl N-($C_1$–$C_3$)alkylamide. The amide is then reacted with phosgene in the presence of a tertiary amine such as pyridine to form the intermediate N-($C_1$–$C_3$ alkyl)-N-chlorocarbonyl amide derivative which on reaction with tetramethylguanidinium azide provides 1-(1-methyl-1H-tetrazole-5-ylmethyl)-5-chloro-1H-tetrazole. The latter is converted to the 5-thiol with sodium hydrosulfide.

The 2H-tetrazole represented by the above formula B wherein R is hydrogen, namely, 2-(1H-tetrazole-5-ylmethyl)-2H-tetrazole-5-thiol, is prepared by reacting 5-benzylthio-2-cyanomethyl-2H-tetrazole with tetramethylguanidinium azide or with aluminum triazide followed by electrolytic reduction to remove the benzyl group. The cyanomethyl tetrazole starting material is prepared by reacting 5-benzylthio-1H-tetrazole with chloroacetonitrile in the presence of base. The mixture of the isomeric 1 and 2-cyanomethyl derivatives is separated and the 2-isomer reacted with the azide as described above. Alternatively, the mixture of the 1- and 2-cyanomethyl derivatives is reacted with the azide and the isomeric bis-tetrazolemethyl products is separated.

The bis-tetrazolemethyl compounds of the invention are used in the preparation of broad spectrum cephalosporin antibiotics described in copending application Ser. No. 187,859 filed this even date.

DETAILED DESCRIPTION

The tetrazole thiol compounds of this invention are represented by the following formulas

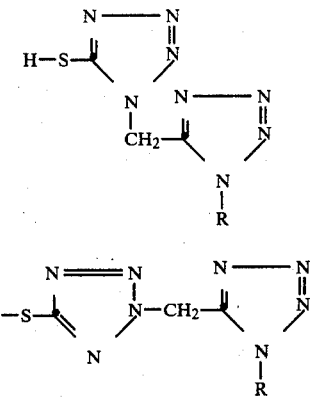

wherein each R is hydrogen or $C_1$–$C_3$ alkyl.

As shown in the above formulas, the compounds are characterized by a 1H-tetrazole ring bonded through a methylene group to 1H- or 2H-tetrazole-5-thiol group. For convenience, the compounds are referred to herein as bis-tetrazolemethyl thiols. They are formally named as follows: 1-(1H-tetrazole-5-ylmethyl)-1H-tetrazole-5-thiol, or the $C_1$–$C_3$ alkyl derivative, and 2-(1H-tetrazole-5-ylmethyl)-2H-tetrazole-5-thiol, or the $C_1$–$C_3$ alkyl derivative.

Examples of the bis-tetrazolemethyl compounds are 1-(1H-tetrazole-5-ylmethyl)-1H-tetrazole-5-thiol, 1-(1-methyl-1H-tetrazole-5-ylmethyl)-1H-tetrazole-5-thiol, 1-(1-ethyl-1H-tetrazole-5-ylmethyl)-1H-tetrazole-5-thiol, 1-(1-n-propyl-1H-tetrazole-5-ylmethyl)-1H-tetrazole-5-thiol, 2-(1H-tetrazole-5-ylmethyl)-2H-tetrazole-5-thiol, and 2-(1-methyl-1H-tetrazole-5-ylmethyl)-2H-tetrazole-5-thiol.

The 1-(1H-tetrazole-5-ylmethyl)-1H-tetrazole-5-thiol represented by the above formula A wherein R is hydrogen is prepared by reacting 1-cyanomethyl-1H-tetrazole-5-thiol with tetramethylguanidinium azide (TMGA) as shown in the following reaction scheme:

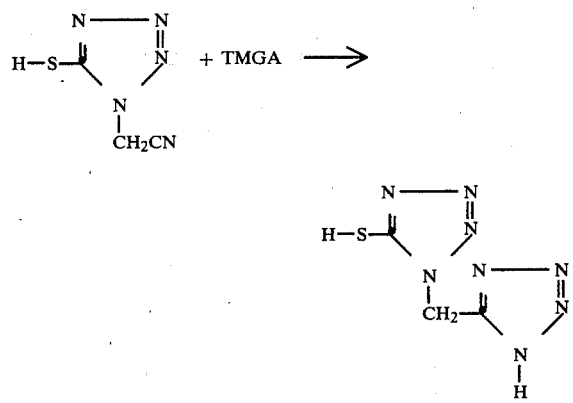

The reaction is carried out by heating a solution of the cyanomethyl tetrazole thiol with TMGA until the reaction is complete. Excess TMGA is preferably employed and about a 1.5 to 2.0 molar excess is best used. Solvents which can be used are, for example, dioxane, toluene, and chlorobenzene. The reaction proceeds at a satisfactory rate at elevated temperatures of from about 95° C. to about 125° C.

The TMGA is prepared by the procedure described in Fieser and Fieser, *Reagents for Organic Synthesis*, Vol. 2, pp 403–404, Wiley-Interscience, N.Y. 1969.

In an example of the preparation of 1-(1H-tetrazole-5-ylmethyl)-1H-tetrazole-5-thiol, one mole of 1-cyanomethyl-1H-tetrazole-5-thiol is dissolved in 500 ml of dioxane and 1.5 moles of TMGA are added. The solution is heated at the reflux temperature with stirring for about 5 hours. The product is isolated by evaporating the mixture to dryness, and the reaction product mixture is taken up in a mixture of water and a water immiscible organic solvent such as ethyl acetate. The aqueous layer is separated and acidified to a pH below pH 2 and the product is extracted with an organic solvent such as ethyl acetate. The extract is washed, dried, and evaporated to dryness to yield the product.

The 1-cyanomethyl-1H-tetrazole-5-thiol used in the above preparation is prepared as follows. Ethyl azidoacetate is heated at a temperature of about 125° C. with an excess of cyanogen chloride to form 5-chloro-1H-tetrazole-1-ylacetate as a crystalline solid. The latter product is converted to the 5-thiol by heating the 5-chloro tetrazole with sodium hydrosulfide in an organic solvent such as ethyl alcohol. The reaction is carried out satisfactorily at the reflux temperature in ethyl alcohol for about 20–24 hours. The thiol is recovered by concentrating the reaction mixture and extracting with an organic solvent, for example, ethyl acetate.

The ethyl 5-thiol-1H-tetrazole-1-ylacetate product is then converted to the amide by heating the 5-thiol ester in a mixture of concentrated ammonium hydroxide, ammonium chloride and ethyl alcohol. The amide is recovered as the ammonium salt. The amide, 5-thiol-1H-tetrazol-1-ylacetamide ammonium salt, is then dehydrated to 1-cyanomethyl-1H-tetrazol-5-thiol. The dehydration of the amide is carried out by heating a solution of the amide in an inert organic solvent with a dehydrating agent in the presence of a hydrogen halide acceptor.

The dehydration of the amide in the last step of the reaction scheme can be carried out in an inert organic solvent such as a halogenated hydrocarbon solvent for example, methylene chloride, chloroform, a di- or trichloroethane, such as 1,2-dichloroethane and 1,1,2-trichloroethane.

Dehydrating agents which can be used in preparing the 1-cyanomethyl tetrazole include phosphorus oxychloride, phosphorus pentachloride, phosphorus pentoxide or thionyl chloride. Phosphorus oxychloride is the preferred dehydrating agent.

The preparation of the cyanomethyl tetrazole 5-thiol is illustrated in the following reaction scheme.

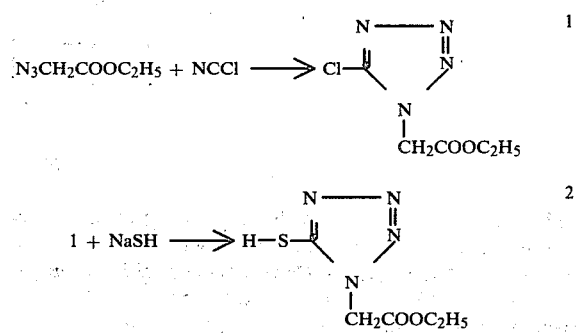

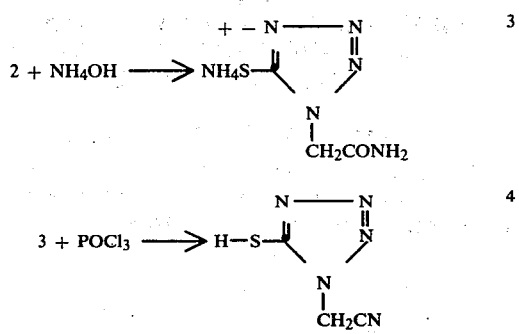

The tetrazole compounds of the formula A wherein R is $C_1$–$C_3$ alkyl are prepared with 5-chloro-1H-tetrazole-1-ylacetate ester as follows. The 5-chloro tetrazole ester is reacted with a $C_1$–$C_3$ alkyl primary amine to form the N-($C_1$–$C_3$ alkyl) 5-chloro-1H-tetrazol-1-ylamide. The amide is reacted with phosgene to form the intermediate N-chlorocarbonyl amide of the 5-chloro tetrazole, and the latter with TMGA to provide the 5-chloro-1-[1-($C_1$–$C_3$ alkyl)-1H-tetrazol-5-ylmethyl]-1H-tetrazole. The 5-chloro-bis-tetrazole is then reacted with sodium hydrosulfide to provide the corresponding 5-thiol. The following reaction scheme illustrates the above sequence of reactions.

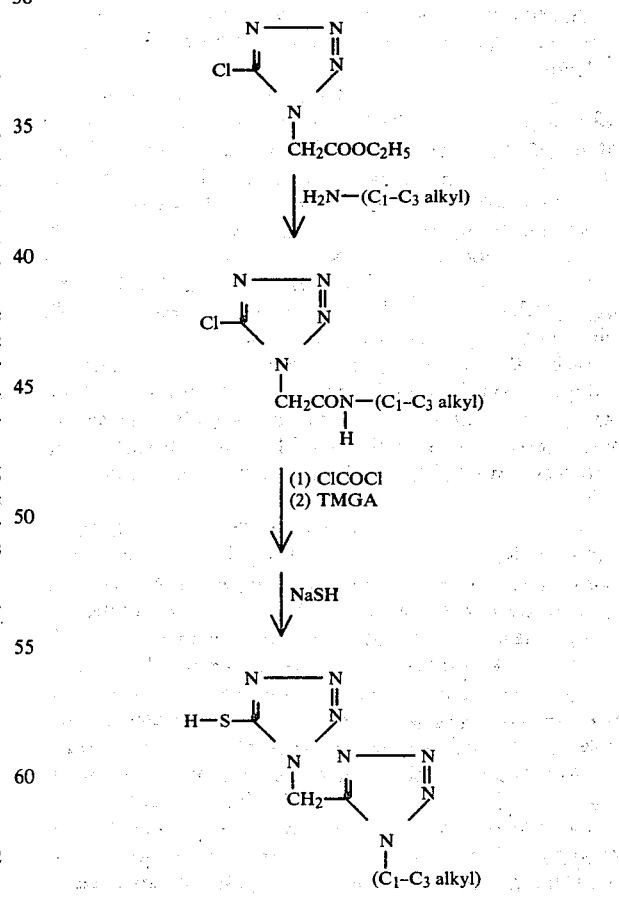

In the first step of the above preparative scheme, the 5-chloro tetrazole ester, for example ethyl 5-chloro-1H-tetrazol-1-ylacetate, is dissolved in ethyl alcohol and the solution is cooled to 0° C. or below. Excess primary amine is added to the cold solution with stirring. Amines which are used are methylamine, ethylamine, n-propylamine and iso-propylamine. The amide formation is rapid and the product usually crystallizes from the reaction mixture.

The 5-chloro tetrazole secondary amide is then reacted at about 0° C. in an inert solvent such as methylene chloride with excess phosgene in the presence of pyridine to form the N-chlorocarbonyl amide. The reaction mixture is evaporated to dryness and the reaction product mixture is suspended in dioxane and excess TMGA is added to the solution. The reaction mixture is heated at the reflux temperature for about two hours to form the 5-chloro N-($C_1$-$C_3$ alkyl)bis-tetrazolemethyl compound. The latter is then heated with sodium hydrosulfide at a temperature between about 55° C. and about 85° C. to form the corresponding 5-thiol. Ethyl alcohol is a suitable solvent in which to carry out the 5-thiol preparation.

In a similar manner, other alkyl esters of azidoacetic acid can be used in the reaction scheme. For example, the $C_1$-$C_4$ alkyl esters such as the methyl, ethyl, n-propyl, n-butyl, and isobutyl esters.

The 2-(1H-tetrazole-5-ylmethyl)-2H-tetrazol-5-thiol and the 1-($C_1$-$C_3$ alkyl) derivatives thereof represented by the Formula B are prepared as follows. In general, a tetrazole-5-thiol wherein the thiol is protected with a thiol-protecting group is alkylated with chloroacetonitrile or bromoacetonitrile in the presence of a base in an inert solvent to provide a mixture comprising approximately equal amounts of the 1- and 2-cyanomethyl isomers. Bases which can be used include for example, the alkali metal hydroxides and carbonates such as potassium hydroxide, sodium hydroxide, potassium carbonate and sodium carbonate. Solvents which can be used are the alkanols such as the $C_1$-$C_4$ alkanols, for example, methanol, ethanol, propanol and butanol; the nitriles such as acetonitrile and propionitrile; amides such as dimethylformamide, dimethylacetamide, N-methylpyrrolidone and the like; ethers such as tetrahydrofuran, dioxane and the like; or other convenient organic solvent which is inert under the conditions of the reaction.

The alkylation can be carried out at a temperature between about 15° C. to about 75° C. and is conveniently carried out at or near room temperatures.

Thiol protecting groups which can be used to block the 5-thiol group during the alkylation are any readily removed thiol-protecting group which is stable under the basic conditions of the alkylation reaction. Examples of protecting groups are the arylmethyl groups such as benzyl and diphenylmethyl and the substituted benzyl and diphenylmethyl groups such as 4-methylbenzyl, 4-methoxybenzyl, 4-nitrobenzyl, 3- or 4-chlorobenzyl, 4-methoxybenzhydryl, and 4,4'-dimethoxybenzhydryl. The benzyl group is a preferred thiol protecting group.

The 1H-tetrazole-5-thiol wherein the thiol group is protected, for example 5-benzylthio-1H-tetrazole, is prepared by heating thiosemicarbazide with a benzylic halide or with a diphenylmethyl halide, for example the chloride or bromide, in ethyl alcohol to obtain the intermediate S-benzyl or S-benzylhydryl hydrobromide or hydrochloride of the formula

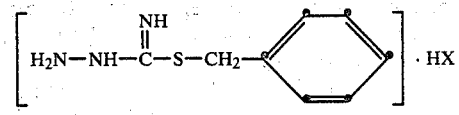

wherein X is chloro or bromo.

The S-benzyl salt is recovered by evaporating the reaction mixture to dryness, dissolving the residue in water, and washing the aqueous solution with a water immiscible solvent such as ethyl acetate. The aqueous solution of the S-benzyl salt is then treated with an excess of sodium or potassium nitrite at room temperature to provide the 5-protected-thio-1H-tetrazole for example, 5-benzylthio-1H-tetrazole. The product is recovered from the aqueous reaction mixture by extraction with a water immiscible organic solvent such as ethyl acetate.

The 5-protected-thio-1H-tetrazole is then alkylated as described above to provide the 1- and 2-cyanomethyl-1H-tetrazole-5-protected thiol. The cyanomethyl tetrazole is reacted with an azide reagent, for example aluminum triazole or TMGA to form the isomeric 1- and 2-(1H-tetrazole-5-ylmethyl)tetrazole-5-protected thiols.

The reaction of the azide agent with the cyanomethyl tetrazole is carried out at a temperature between about 75° C. and about 150° C. in an aprotic organic solvent, for example an ether such as dioxane, the dimethyl ether of ethylene glycol, diglyme or like solvents. The bis-tetrazole is recovered from the reaction mixture, following concentration in vacuo, by extraction with ethyl acetate.

The isomeric bis-tetrazoles are obtained in most instances as an oil from which are obtained on standing the crystalline 2-isomer. The crystalline-oil mixture of isomers is separated conveniently by trituration of the mixture with methylene chloride or diethyl ether.

The 2-isomer is identified and distinguished from the 1-isomer conveniently by its nmr spectrum. The two protons of the methylene group bonding the two tetrazole rings show a signal at about 6.45 ppm for the 2-isomer, while the corresponding signal of the 1-isomer occurs at about 6.03 ppm.

The 5-thiol protecting group of 2-(1H-tetrazole-5-ylmethyl)tetrazole-5-thiol is conveniently removed by electrolytic reduction. Prior to reduction a small sample is analyzed polarographically to determine the reduction potential in a conventional polarograph.

In an example of the electrolytic reduction, 5-benzylthio-2-(1H-tetrazole-5-ylmethyl)tetrazole is dissolved in distilled dimethylformamide and the solution is placed in an electrolytic cell. A suitable electrolyte such as a tetraalkyl ammonium perchlorate for example, tetrabutyl or tetraethylammonium perchlorate is used with a platinium wire anode and a mercury pool cathode separated by a glass frit. A standard calomel electrode is employed as with most electrolytic reductions. The reduction is carried out at a temperature between about 15° C. and about 35° C. at a potential of −2.7 to about −2.85 v.

The thiol product is recovered from the reduction product mixture by evaporating the mixture under reduced pressure, dissolving the residue in ethyl acetate, filtering if necessary, thoroughly washing the ethyl acetate solution with 1 N hydrochloric acid, drying the solution, and evaporating the solution to dryness.

The 2-(1H-tetrazole-5-ylmethyl)tetrazole-5-thiol can be used, as recovered, in the preparation of the cephalosporin antibiotics, or the compound can be purified by recrystallization prior to use.

The bis-tetrazole thiols represented by the formula B wherein R is $C_1$-$C_3$ alkyl are prepared by alkylating the 5-protected-thio-1H-tetrazole with a $C_1$-$C_3$ alkyl halide, for example the alkyl iodide or alkyl bromide. Following alkylation the 5-thiol protecting group is cleaved by electrolysis as described above. The alkylation is carried out by first converting the 1H-tetrazole to the salt form with a suitable base such as sodium or potassium hydroxide in an alcohol such as a $C_1$-$C_4$ lower alkanol, for example methyl alcohol or ethyl alcohol. The alkyl halide is added to the mixture to provide the N-alkyl tetrazole.

As with the alkylation described above to form the cyanomethyl derivative, the alkylation affords a mixture of the 1- and 2-alkyl isomers. The isomers are separated by crystallization or chromatography over silica gel.

Examples of alkyl iodides which are used in the alkylation are methyl iodide, ethyl iodide, n-butyl iodide, and isopropyl iodide. Alkyl bromides and chlorides can also be used; however, the iodides are preferred owing to their greater reactivity.

The above described preparation of 2-(1H-tetrazole-5-ylmethyl)tetrazole-5-thiol is shown in the following reaction scheme

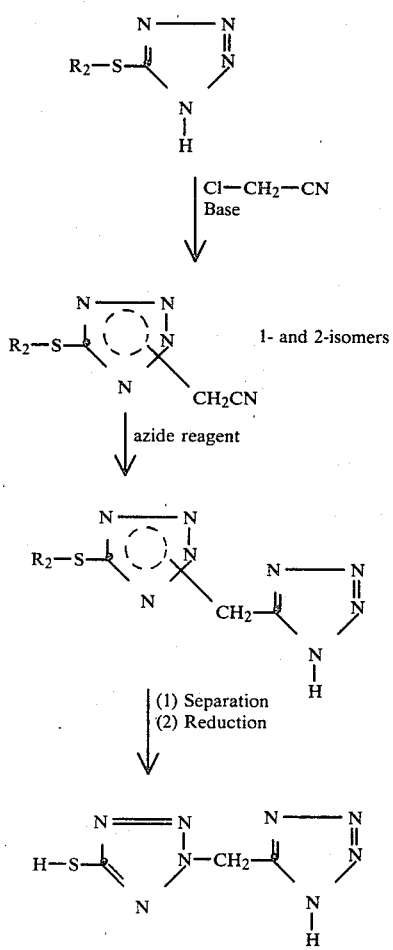

wherein $R_2$ is a base stable thiol protecting group.

The bis-tetrazolemethyl compounds of this invention are useful intermediates in the preparation of broad spectrum cephalosporin antibiotics as described in copending application Ser. No. 187,859 filed this even date. For example, 1-(1H-tetrazole-5-ylmethyl)-1H-tetrazole-5-thiol is reacted with a 7-acylaminocephalosporanic acid to provide the corresponding 7-acylamino-3-[1-(1H-tetrazole-5-ylmethyl)-1H-tetrazole-5-ylthiomethyl]-3-cephem-4-carboxylic acid. For example, a bis-tetrazolemethyl compound of the invention is reacted with the cephalosporin antibiotic, cephalothin, to provide the 7-(2-thienylacetamido)-3-cephem-4-carboxylic acid wherein a bis-tetrazolemethyl thiol of the formula A or the formula B is bonded via the sulfur atom at the methylene group in the 3-position of the cephem nucleus.

Alternatively, the substituted cephalosporin antibiotics can be prepared by reacting a bis-tetrazolemethyl compound of the invention with 7-aminocephalosporanic acid to form the 7-amino-3-(bis-tetrazolemethylthiomethyl)-3-cephem-4-carboxylic acid. The latter can be acylated at the basic 7-amino group to form the desired 7-acylamino-3-(bis-tetrazolemethylthiomethyl)-3-cephem-4-carboxylic acid antibiotic compound. For example, 7-aminocephalosporanic acid is reacted in glacial acetic acid with 1-(1H-tetrazole-5-ylmethyl)-1H-tetrazole-5-thiol or with 2-(1H-tetrazole-5-ylmethyl)-2H-tetrazole-5-thiol to provide the corresponding 7-amino-3-(bis-tetrazolemethylthiomethyl)-3-cephem-4-carboxylic acid. The 3-substituted nucleus compounds are represented by the formula

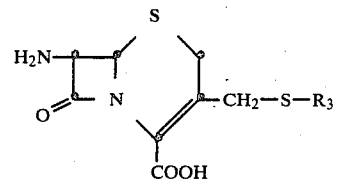

wherein $R_3$ is a bis-tetratrolemethyl group of the formulas

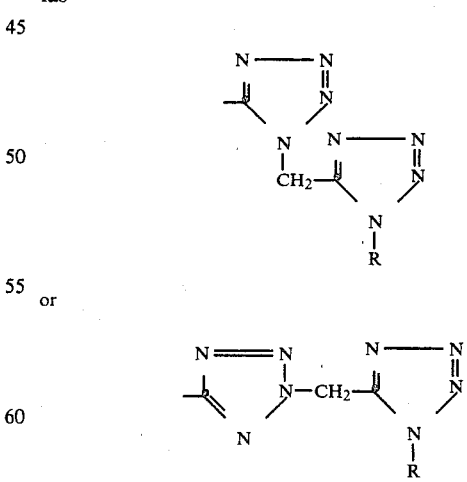

wherein R is hydrogen or $C_1$-$C_3$ alkyl.

The above bis-tetrazolemethyl substituted nucleus compounds are intermediates which can be acylated with the desired carboxylic acid to provide the 7-acylaminocephalosporin antibiotics as described in copending application Ser. No. 187,859. For example, a 7-amino nucleus compound represented by the above formula or an ester thereof is reacted in an inert organic solvent such as acetonitrile with the mixed anhydride derivative of 2-thiopheneacetic acid formed with methyl chloroformate or isobutyl chloroformate, to provide the N-acylated derivative 7-(2-thienylacetamido)-3-(bis-tetrazolemethylthiomethyl)-3-cephem-4-carboxylic acid or an ester thereof.

Also, the bis-tetrazolemethyl thiols can be reacted with 3-halomethylcephalosporin esters to provide esters of the 3-(bis-tetrazolemethyl)substituted cephalosporins described in the above-identified copending application. For example, p-nitrobenzyl 7-(2-thienylacetamido)-3-bromomethyl-3-cephem-4-carboxylate is reacted with a bis-tetrazolemethyl thiol of the invention in a suitable organic solvent such as dimethylformamide or dimethylacetamide to provide p-nitrobenzyl 7-(2-thienylacetamido)-3-(bis-tetrazolemethylthiomethyl)-3-cephem-4-carboxylate. Deesterification of the p-nitrobenzyl ester with zinc and acetic acid, with hydrogen in the presence of 5% palladium on carbon catalyst, or by electrochemical reduction, affords the substituted cephalosporin as the free acid antibiotic compound.

This invention also provides the novel intermediate to the bis-tetrazolemethyl thiols represented by the above formula A. The intermediate, 1-cyanomethyl-1H-tetrazole-5-thiol, is represented by the formula

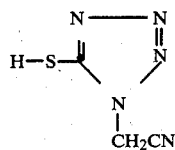

and is prepared as described above by the dehydration of the corresponding amide.

The 1-cyanomethyltetrazole-5-thiol is also useful in the preparation of 7-amino- and 7-acylamino-3-(1-cyanomethyltetrazole-5-ylthiomethyl)-3-cephem-4-carboxylic acid antibiotics as described in copending application Ser. No. 187,860 filed this even date. The thiol is used in the preparation of the cephalosporins by the same methods described above for the bis-tetrazolemethyl substituted cephalosporins. For example, a 7-amino or 7-acylaminocephalosporanic acid is reacted in a non-aqueous medium with 1-cyanomethyl-1H-tetrazole-5-thiol to provide the 7-amino-3-(1-cyanomethyl-1H-tetrazole-5-ylthiomethyl)-3-cephem-4-carboxylic acid or the corresponding 7-acylamino compound. The 7-amino-3-cephem product can be N-acylated by known procedures with the desired carboxylic acid or an active derivative thereof to provide the 7-acylamino cephalosporin.

The following examples are provided to further illustrate the invention.

In the following preparations and examples, unless otherwise specified, the nmr spectra were run on a Varian Associates Model T-60 Spectrometer. In the description of the nmr spectra, s=singlet, d=doublet, q=quartet, and m=multiplet. Melting points are uncorrected.

PREPARATION OF 1-CYANOMETHYL-1H-TETRAZOL-5-YLTHIOL

A. Ethyl azidoacetate

To a solution of 490 g. (4 moles) of ethyl chloroacetate in 1500 ml. of acetonitrile were added 260 g. (4 moles) of sodium azide, and the mixture was heated at the reflux temperature for 20 hours. After heating, the reaction mixture was poured into 1 liter of water with stirring for ½ hour. The organic phase was separated from the aqueous phase and evaporated in vacuo to dryness. The yellow residual oil was dissolved in 1200 ml. of diethyl ether and the solution was dried over magnesium sulfate. Evaporation of the diethyl ether in vacuo gave 391 g. (76% yield) of ethyl azidoacetate.

B. Ethyl 5-chloro-1H-tetrazol-1-ylacetate

A mixture of 130 g. (1 mole) of ethyl azidoacetate prepared as described in part A and 96 g. (1.56 mole) of cyanogen chloride was heated at a temperature of 125° C. for 20 hours. After the reaction mixture had cooled, the reaction product mixture was dissolved in ethyl acetate, and the solution was filtered and evaporated in vacuo yielding a yellow crystalline mass of product. The yellow crystals were recrystallized from aqueous ethyl alcohol and gave 149 g. (78% yield) of ethyl 5-chloro-1H-tetrazol-1-ylacetate as pale yellow crystals melting at about 57°-60° C.

C. Ethyl 5-thiol-1H-tetrazol-1-ylacetate

A solution of 209 g. of the chlorotetrazole ester, prepared as described in part B above, and 250 g. of sodium hydrosulfide in 5 liters of ethyl alcohol was heated at the reflux temperature for 24 hours. After heating, the reaction mixture was acidified with concentrated hydrochloric acid, and the volume of the acidified mixture was reduced to ¼ the original volume by evaporation in vacuo. The concentrate was extracted with ethyl acetate, the extract was dried and evaporated to dryness under reduced pressure. The residual product was recrystallized from toluene-methylene chloride-hexane and gave 129 g. of the product melting at about 85° C. to 88° C.

D. 5-Thiol-1H-tetrazol-1-ylacetamide ammonium salt

A solution of 20 g. (0.106 mole) of the tetrazolthiol ester, prepared as described above in part C, in 320 ml. of concentrated ammonium hydroxide and 200 ml. of ethyl alcohol containing 500 ml. of ammonium chloride was heated at the reflux temperature for about 12 hours. After heating, the reaction mixture was evaporated in vacuo, and the yellow crystalline residue obtained was recrystallized from hot ethyl alcohol to yield a first crop of 13.7 g. (73% yield) of the product as white crystals melting at about 197° to about 199° C. after vacuum drying. A second crop of 1.4 g. of the product was obtained which melted at about 191°-193° C.

E. 1-Cyanomethyl-1H-tetrazol-5-thiol

A suspension of 5.28 g. of the tetrazolamide ammonium salt, prepared as described above in part D, in 90 ml. of methylene chloride containing 14.4 ml. of pyridine was cooled to a temperature of about 0° C. To the suspension was added dropwise with stirring a solution of 4.6 g. (30 mmole) of phosphorous oxychloride in 40 ml. of methylene chloride. After the addition was completed, the reaction mixture was heated at the reflux temperature for 30 minutes and was then cooled to room temperature with stirring. The reaction mixture had turned orange after heating and contained some precipitate. The reaction mixture was evaporated to dryness in vacuo and the residue dissolved in ethyl acetate-water, 1:1, v:v. The pH of the solution was adjusted to pH 2 with 20% aqueous hydrochloric acid. The acidified solution was then extracted twice with 75 ml. portions of ethyl acetate and the extracts combined. The extract was then washed with 5% hydrochloric acid, with brine, was dried over sodium sulfate and evaporated in vacuo. The brown oil obtained as a residue crystallized on standing. The crystals were vacuum dried at room temperature and yielded after drying 2.6 g. (61% yield) of light brown product melting at about 113°–114° C.

The above reaction was repeated on a 10.6 g. batch of the tetrazol amide ammonium salt and 3.7 g. of the nitrile as off-white crystals melting at about 116°–118° C. was obtained.

The following analytical data were obtained for the crystalline product.

Elemental analysis calculated for $C_3H_3N_5S$: Theory: C, 25.53; H, 2.14; N, 49.62. Found: C, 25.82; H, 2.40; N, 49.91.

The mass spectrum of the crystalline product showed a molecular weight of 141 in agreement with the product.

EXAMPLE 1

1-(1H-Tetrazol-5-ylmethyl)-1H-tetrazol-5-thiol

A solution of 6.0 g. (42.5 mmole) of 1-cyanomethyl-1H-tetrazol-5-thiol and 10.0 g. (6.3 mmole) of tetramethylguanidinium azide in 90 ml. of dioxane was heated at the reflux temperature for 3 hours. After cooling, the reaction mixture was evaporated to dryness in vacuo and the residue dissolved in ethyl acetate:water, 1:1. The ethyl acetate layer was separated, and the pH of the aqueous layer was adjusted to pH 1.8 with 20% hydrochloric acid. The acidified aqueous layer was then extracted 3 times with 75 ml. portions of ethyl acetate, and the extracts were combined. The extract was washed with 5% hydrochloric acid, with brine, was dried over sodium sulfate, and then evaporated in vacuo to dryness. The red oil obtained as a residue crystallized on seeding. The crystals were washed with ethyl acetate and with diethyl ether and were dried. There were obtained 3.7 g. of the bis-tetrazolmethyl thiol melting at about 173° C. to about 175° C. The filtrate from the first crop was evaporated to an oil and after seeding the oil, 0.3 g. of a second crop crystalline product were obtained. A third crop of 0.3 g. was obtained in the same manner. Total yield of product was 4.3 g. (55% yield).

The NMR spectrum of the product run in DMSO-$d_6$ showed a singlet at 5.9 ppm delta for the protons of the methylene group bridging the tetrazole rings.

EXAMPLE 2

1-(1-Methyl-1H-tetrazol-5-ylmethyl)-1H-tetrazol-5-thiol

A. N-Methyl-5-chloro-1H-tetrazol-1-yl-acetamide

A solution of 19.5 g. (0.102 mole) of ethyl 5-chloro-1H-tetrazol-1-acetate in 30 ml. of ethyl alcohol was cooled in a dry ice-propyl alcohol bath, and methylamine gas were passed into the solution for 5 minutes. The reaction mixture solidified and was washed with ethyl alcohol and diethyl ether and was dried on the steam bath. There were obtained 13.2 g. (74% yield) of the N-methylamide product as white crystalline needles melting at about 146° to 148° C.

The following analytical data were obtained for the crystalline product.

Elemental analysis calculated for $C_4H_6N_5OCl$: Theory: C, 27.36; H, 3.44; N, 39.89; Cl, 20.19. Found: C, 27.59; H, 3.35; N, 39.65; Cl, 20.49.

NMR (DMSO-$d_6$): δ2.7 (d, J=5 Hz, 3H, amide methyl), 5.28 s, 2H, $CH_2$), 8.53 (s, broad, 1H, N—H) ppm.

Molecular weight via mass spectrum=175.5.

B.

1-(1-Methyl-1H-tetrazol-5-ylmethyl)-5-chloro-1H-tetrazole

To a suspension of 1.75 g. (10 mmole) of 5-chloro-N-methyl-1H-tetrazol-1-acetamide, prepared as described under A above, in 50 ml. of methylene chloride containing 0.8 g. of pyridine and maintained at a temperature of about 0° C. was added with stirring excess phosgene. After addition was complete, the reaction mixture was stirred for 10 minutes without further cooling. The clear solution obtained on reaction was evaporated to dryness at a temperature of about 30° C. under reduced pressure. The residue containing the reaction product was suspended in 50 ml. of dioxane, and 2.4 g. (15.2 mmole) of tetramethylguanidinium azide were added to the suspension. The mixture was heated for 2 hours at the reflux temperature and after stirring overnight at room temperature, the reaction mixture was concentrated to near dryness under reduced pressure. The concentrate was dissolved in 30 ml. of water forming a pale yellow solution from which the product crystalized as colorless needles. The product was filtered and 0.4 g. of the crystalline product melting at about 138° C. to about 140° C. were obtained. A second crop of 0.5 g. of the product melting at about 136° C. to about 139° C. was isolated from the filtrate.

The following analytical data were obtained for the crystalline product.

Elemental analysis calculated for $C_4H_5N_8Cl$: Theory: C, 23.95; H, 2.51; N, 55.86; Cl, 17.45. Found: C, 24.17; H, 2.75; N, 55.81; Cl, 17.85.

NMR (DMSO-$d_6$): δ4.27 (s, 3H, N—$CH_3$), 6.33 (s, 2H, $CH_2$) ppm.

C.

1-(1-Methyl-1H-tetrazol-5-ylmethyl)-1H-tetrazol-5thiol

To a suspension of 0.5 g. (2.5 mmole) of the 5-chloro-bis-tetrazole, prepared as described in B above, in 40 ml. of ethyl alcohol was added 0.6 g. of sodium hydrosulfide. The mixture was heated at the reflux temperature for 16 hours, was cooled to room temperature, and filtered. The filtrate was concentrated to near dryness under reduced pressure and 30 ml. of 5% hydrochloric acid were added. The acidified concentrate was extracted 3 times with 30 ml. portions of ethyl acetate, and the extracts were combined and washed with 5% hydrochloric acid, brine, and dried over sodium sulfate. The dried extract was concentrated to a small volume from which the crystalline product precipitated. The product was recrystallized from ethyl acetate-hexane, and there was obtained 0.3 g. of the product as nearly colorless crystals melting at about 190° C. to about 192° C.

The following analytical data were obtained for the crystalline product.

Elemental analysis calculated for $C_4H_6N_8S$: Theory: C, 24.24; H, 3.05; N, 56.53. Found: C, 24.21; H, 3.28; N, 56.43.

NMR (DMSO-$d_6$): δ4.22 (s, 3H, $CH_3$), 5.95 (s, 2H, $CH_2$), 10.57 (broad s, 1H, SH).

The molecular weight as determined by mass spectrum was 198.

EXAMPLE 3

2-(1H-Tetrazole-5-ylmethyl)-tetrazole-5thiol

A. 5-Benzylthio-1H-tetrazole

A solution of 30 g. (0.33 mole) of thiosemicarbazide and 51 g. (0.40 mole) of benzyl chloride in 500 ml. of ethyl alcohol was heated at the reflux temperature for about 3.5 hours. After heating, the reaction mixture was evaporated to dryness under reduced pressure and the residue was dissolved in water. The solution was washed with ethyl acetate and was added to a solution of 25 g. (0.36 mole) of sodium nitrite in 50 ml. of water. The solution was stirred for 15 minutes and then ethyl acetate was added. The organic layer was separated and washed with water, brine, and was dried over sodium sulfate. The dried ethyl acetate solution was evaporated under reduced pressure, and the product obtained as a residue was washed with methylene chloride and recrystallized from ethyl acetate. There were obtained 21 g. of the product melting at about 134° C. to about 136° C.

The following elemental analysis was obtained for the product.

Elemental analysis calculated for $C_8H_8N_4S$: Theory: C, 49.98; H, 4.19; N, 29.14. Found: C, 49.81; H, 4.17; N, 28.95.

B. 1- and 2-Cyanomethyl-5-benzylthio-1H-tetrazole

A solution of 2.7 g. of potassium hydroxide in 5 ml. of methyl alcohol was added with stirring to a solution of 7.9 g. (0.041 M) of 5-benzylthio-1H-tetrazole in 25 ml. of methyl alcohol, and after stirring the solution for 15 minutes at room temperature, 3.4 g. (0.045 M) of chloroacetonitrile were added. The reaction mixture was heated at the reflux temperature for about 12 hours and the white solid which formed was filtered. The filtrate was concentrated in vacuo to an oily residue, and the residue dissolved in a mixture of diethyl ether and water. The ether layer was separated and washed with an aqueous solution of sodium bicarbonate, water, and with brine, and was dried and evaporated to dryness under reduced pressure. There were obtained 3.4 g. of a mixture of 1- and 2-cyanomethyl-5-benzylthio-1H-tetrazole as a reddish oil. The NMR spectrum of the oil showed it was a mixture containing approximately 50% of each of the isomers.

C.
5-Benzylthiol-2-(1H-tetrazol-5-ylmethyl)-2H-tetrazole

To 70 ml. of dry tetrahydrofuran cooled in an ice-ethanol bath were added in small portions 4.04 g. (0.03 mole) of anhydrous aluminum chloride. After addition was complete, 5.85 g. (0.09 mole) of finely ground sodium azide were added with stirring. After stirring the mixture for 5 minutes, a solution of 3.93 g. (0.017 mole) of the 1- and 2-cyanomethyl-5-benzylthio-tetrazole isomeric mixture in 20 ml. of dry tetrahydrofuran was added and the mixture heated at the reflux temperature for 24 hours. The reaction mixture was cooled in an ice-ethanol mixture and acidified by dropwise addition of 30 ml. of 20% hydrochloric acid. The acidified mixture was concentrated under reduced pressure to a volume of about 30 ml., and the concentrate was extracted with three 30 ml. portions of ethyl acetate. The extracts were combined, washed with brine, and dried over anhydrous sodium sulfate. The dried extract was evaporated under vacuum to dryness providing 4.5 g. (97% yield) of a mixture of the isomeric 5-benzylthio-1- and 2-(1H-tetrazole-5-ylmethyl)-1H- and 2H-tetrazoles as a tan oil. After standing for several days, crystals formed in the oil. The mixture was triturated with methylene chloride and filtered to provide 0.85 g. of cream colored crystals melting at about 115° C. to about 117° C. A second crop of crystals which weighed 0.2 g. was obtained from the filtrate.

The above preparation was repeated by reacting 7.1 g. of the isomeric 5-benzylthio-1- and 2-cyanomethyl-tetrazole with aluminum azide (formed as described above with 7.3 g. of aluminum chloride and 10.7 g. of sodium azide). After heating at the reflux temperature for 24 hours, the reaction mixture was acidified with 20% hydrochloric acid, evaporated to a volume of about 60 ml., extracted with ethyl acetate, the extract washed with brine, dried, and evaporated to dryness. The residue crystallized on standing. The cream colored crystals were suspended in methylene chloride and filtered to provide 3.5 g. of cyrstalline material. The filtrate was evaporated to dryness to provide 4.9 g. of orange oil.

The nmr spectrum of the crystalline product run in deuterated DMSO showed mainly one isomer, the 2-isomer, while the nmr spectrum of the oil showed mainly the 1-isomer.

D. 2-(1H-Tetrazole-5-ylmethyl)-2H-tetrazole-5-thiol

5-Benzylthio-2-(1H-tetrazole-5-ylmethyl)-2H-tetrazole, 175 mg., prepared as described above under part C, was dissolved in 40 ml. of distilled DMF and reduced at the mercury pool cathode (14 $cm^2$ Hg pool) with a platinium wire anode. The electrodes were separated by a glass frit. The electrolyte was tetraethylammonium perchlorate, 0.1 M in the DMF solution of the substrate. The electrolysis was carried out at −2.7 to −2.85 volts for 500 seconds and at −2.80 v. for about 630 seconds.

The reduction product mixture from the one-electron reduction was evaporated to dryness and the residue of product dissolved in ethyl acetate. The solution was washed three times with a 9:1 by volume mixture of a saturated solution of sodium chloride and 0.1 N hydrochloric acid and was dried over anhydrous magnesium sulfate. The dried solution was concentrated in vacuo and 111 mg. of the title compound precipitated from the concentrate. The product was filtered and dried.

We claim:

1. A compound selected from the group consisting of a compound of the formula

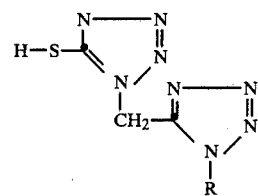

and a compound of the formula
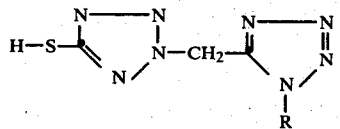
wherein each R is hydrogen or $C_1$–$C_3$ alkyl.
2. The compound of claim 1 of the formula
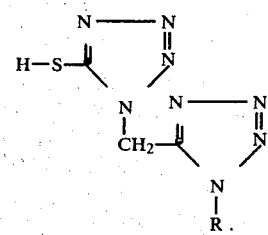
3. The compound of claim 2 wherein R is hydrogen.
4. The compound of claim 2 wherein R is methyl.
5. The compound of claim 1 of the formula
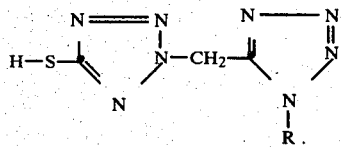
6. The compound of claim 5 wherein R is hydrogen.
7. The compound of the formula
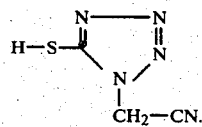
* * * * *

Disclaimer 4,338,452.—*Allen S. Katner*, and *Stephen J. Bogard*, Indianapolis, Ind. 1-AND 2-(1-ALKYL-1H-TETRAZOL-5-YL-METHYL)-1H-TETRAZOL-5-THIOLS AND 1-CYANOMETHYL TETRAZOLE-5-THIOL. Patent dated July 6, 1982. Disclaimer filed June 13, 1983, by the assignee, *Eli Lilly and Co.*

Hereby enters this disclaimer to claim 7 of said patent.
[*Official Gazette August 16, 1983.*]